US007459272B2

(12) United States Patent
Morris et al.

(10) Patent No.: US 7,459,272 B2
(45) Date of Patent: Dec. 2, 2008

(54) REDUCTION IN BACTERIAL COLONIZATION BY ADMINISTERING BACTERIOPHAGE COMPOSITIONS

(75) Inventors: J. Glenn Morris, Baltimore, MD (US); Alexander Sulakvelidze, Baltimore, MD (US); Zemphira Alavidze, Tbilisi (GE); Gary R. Pasternack, Baltimore, MD (US); Torrey C. Brown, Severna Park, MD (US)

(73) Assignee: Intralytix, Inc., Baltimore, MD (US)

( * ) Notice: Subject to any disclaimer, the term of this patent is extended or adjusted under 35 U.S.C. 154(b) by 453 days.

(21) Appl. No.: 10/724,900

(22) Filed: Dec. 2, 2003

(65) Prior Publication Data

US 2004/0247569 A1 Dec. 9, 2004

Related U.S. Application Data

(63) Continuation of application No. 09/757,685, filed on Jan. 11, 2001, now abandoned.

(60) Provisional application No. 60/205,240, filed on May 19, 2000, provisional application No. 60/175,416, filed on Jan. 11, 2000, provisional application No. 60/175,415, filed on Jan. 11, 2000, provisional application No. 60/175,377, filed on Jan. 11, 2000.

(51) Int. Cl.
*C12Q 1/68* (2006.01)
*A61K 35/00* (2006.01)
*C12N 1/20* (2006.01)

(52) U.S. Cl. .......................................... 435/6; 424/93.1
(58) Field of Classification Search ........................ None
See application file for complete search history.

(56) References Cited

U.S. PATENT DOCUMENTS

| 4,375,734 | A | 3/1983 | Kozloff et al. |
| 4,891,210 | A | 1/1990 | Norris |
| 4,957,686 | A | 9/1990 | Norris |
| 5,132,221 | A | 7/1992 | Ward et al. |
| 5,612,182 | A | 3/1997 | Pearson et al. |
| 5,641,464 | A | 6/1997 | Briggs, III et al. |
| 5,660,812 | A | 8/1997 | Merril et al. |
| 5,688,501 | A | 11/1997 | Merril et al. |
| 5,766,892 | A | 6/1998 | Merril et al. |
| 5,811,093 | A | 9/1998 | Merril et al. |
| 6,015,816 | A | 1/2000 | Kostyniak et al. |
| 6,056,954 | A | * 5/2000 | Fischetti et al. ............ 424/94.1 |
| 6,121,036 | A | 9/2000 | Ghanbari et al. |
| 6,322,783 | B1 | 11/2001 | Takahashi |
| 2005/0260171 | A1* | 11/2005 | Ghanbari et al. ........... 424/93.6 |

FOREIGN PATENT DOCUMENTS

| DE | 37 14699 | 1/1988 |
| DE | 3714699 | 1/1988 |
| DE | 19 828696 | 2/1999 |
| DE | 198 28 596 A1 | 2/1999 |
| EP | 0 290 295 | 11/1988 |
| EP | 0290295 | 11/1988 |
| EP | 0 414 304 | 2/1991 |
| EP | 0414304 | 2/1991 |
| EP | 0 510 907 | 10/1992 |
| EP | 0510907 | 10/1992 |
| GB | 2 253 859 | 9/1992 |
| GB | 2253859 | 9/1992 |
| JP | 62 123104 | 4/1987 |
| JP | 62-123104 | 6/1987 |
| WO | WO 90/13631 | 11/1990 |
| WO | WO 9013631 | 11/1990 |
| WO | 95 27043 | 10/1995 |
| WO | WO 95/27043 | 10/1995 |
| WO | 97 39111 | 10/1997 |
| WO | WO 97/39111 | 10/1997 |
| WO | 00 69269 | 11/2000 |
| WO | WO 00/69269 | 11/2000 |

OTHER PUBLICATIONS

Barrow et al. Use of Lytic Bacteriophage for Control of Experimental *Escherichia coli* Septicemia and Meningitis in Chickens and Calves. Clinical and Diagnostic Laboratory Immunology. 5(3): 294-298. 1998.*

(Continued)

*Primary Examiner*—David Guzo
*Assistant Examiner*—Michele K. Joike
(74) *Attorney, Agent, or Firm*—Hunton & Williams LLP

(57) ABSTRACT

The present invention provides a method for reducing the risk of bacterial infection or sepsis in a susceptible patient by treating the susceptible patient with a pharmaceutical composition containing bacteriophage of one or more strains which produce lytic infections in pathogenic bacteria. Preferably, treatment of the patient reduces the level of colonization with pathogenic bacteria susceptible to the bacteriophage by at least one log. In a typical embodiment, the susceptible patient is an immunocompromised patient selected from the group consisting of leukemia patients, lymphoma patients, carcinoma patients, sarcoma patients, allogeneic transplant patients, congenital or acquired immunodeficiency patients, cystic fibrosis patients, and AIDS patients. In a preferred mode, the patients treated by this method are colonized with the pathogenic bacteria subject to infection by said bacteriophage.

39 Claims, No Drawings

OTHER PUBLICATIONS

Carlton, R. Phage Therapy: Past History and Future Prospects. Archivum Immunologiae et Therapiae Experimentalis 47: 267-274, 1999.*

Risi et al. Prevention of infection in the immunocompromised host. Am J Infect Control 26: 594-604, 1998.*

Kudva, Indira T., et al., "Biocontrol of *Escherichia coli* O157 with O157-Specific Bacteriophages", Applied and Environmental Microbiology, vol. 65, p. 3767-3773, 1999.

Lenski, Richard E., "Dynamics of Interactions Between Bacteria and Virulent Bacteriphage", Adv. Microb., Ecol., vol. 10, p. 1-44, 1988.

Levin, Bruce R., et al., "Phage Therapy Revisited: The Population Biology of a Bacterial Infection and its Treatment with Bacteriophage and Antibiotics", The American Naturalist, vol. 147, p. 881-898, 1996.

Ochs, Hans D., "Immunologic Responses to Bacteriophage φX 174 in Immunodeficiency Diseases", The Journal of Clinical Investigation, vol. 50, p. 2559-2567, 1971.

Slopek, et al., "Results of Bacteriophage Treatment of Suppurative Bacterial Infections; I. General Evaluation of the Results", Arch. Immunol. Therapiae Exper., vol. 31, p. 267-291, 1983.

Slopek, et al., Results of Bacteriophage Treatment of Suppurative Bacterial Infections: II. Detailed Evaluation of the Results, Arch. Immunol. Therapiae Exper., vol. 31, p. 293-327, 1981.

Slopek, et al., "Results of Bacteriophage Treatment of Suppurative Bacterial Infections; III. Detailed Evaluation of the Results Obtained in Further 150 cases", Ach. Immunol. Therapiae Exper., vol. 32, p. 317-335, 1984.

Slopek, et al., "Results of Bacteriophage Treatment of Suppurative Bacterial Infections; IV. Evaluation of the Results Obtained in 370 cases", Arch. Immunol. Therapiae Exper., vol. 33, p. 219-240, 1985.

Slopek, et al., "Results of Bacteriophage Treatment of Suppurative Bacterial Infections; V. Evauluation of the Results Obtained I Children", Arch. Immunol. Therapiae Exper., vol. 33, p. 241-260, 1985.

Slopek, et al., "Results of Bacteriophage Treatment of Suppurative Bacterial Infections; VI. Analysis of Treatment of Suppurative Staphylococcal Infections", Arch. Immunol. Therapiae Exper., vol. 33, p. 261-275, 1985.

Slopek, et al., "Results of Bacteriophage Treatment of Suppurative Bacterial Infections in the Years 1981-1986", Arch. Immunol. Therapiae Exper., vol. 35, p. 569-584, 1987.

Soothill, J. S., "Bacteriophage Prevents Destruction of Skin Graft by *Pseudomonas aeruginosa*", Burns, vol. 20, p. 209-211, 1994.

Soothill, J.S., "Treatment of Experimental Infections of Mice with Bacteriophages", J. Med. Microbiol., vol. 37, p. 258-261, 1992.

Alavidze, A., et al., "Isolation of Specific Lytic Phages Multidrug Resistant *Pseudomonas aeruginosa*", The American Society for Microbiology, vol. 99, p. 447, 1999. [Abstract Only].

Slopek, S., et al., "Results of Bacteriophage Treatment of Suppurative Bacterial Infections VI. Analysis of Treatment of Supparative Staphylococcal Infections", Database Biosis 'Online, Biosciences Information Services, 1985. [Abstract Only].

Bogovazova, G. G., et al., "Immunobiological Properties & Therapeutic Effectiveness of Preparations from Klebsiella Bacteriophages", Zh. Mikrobiol. Epidemiol. Immunobiol., vol. 3, p. 30-33, 1992. [Abstract Only].

Barrow, P. A., "Bacteriophages Mediating Somatic Antigenic Conversion in *Salmonella cholerae-suis*: their Isolation from Sewage and Other Salmonella Serotypes Processing the Somatic 6 Antigen" *Journal of General Microbiology*, vol. 132, p. 835-837, 1986.

Barrow, et al., "*Salmonellosis*—Prospects for Microbiological Control in Poultry", Avian Pathology, vol. 18, p. 557-561, 1989.

Barrow, Paul A., et al., "Bacteriophage Therpay and Prophylaxis: Rediscovery and Renewed Assessment of Potential", Trends in Microbiology, vol. 5, p. 268-271, 1997.

Berchieri, A., Jr., et al., The Activity in the Chicken Alimentary Tract of Bacteriophages Lytic for *Salmonella typhimurium, Res. Microbiol.*, vol. 142, p. 541-549, 1991.

Williams Smith, H., et al., "Successful Treatment of Experimental *Escherichia coli* Infections in Mice Using Phage: Its General Superiority Over Antibiotics", *Journal of General Microbiology*, vol. 128, p. 307-318, 1982.

Williams Smith, H., et al., "Effectiveness of Phages in Treating Experimental *Escherichia coli* Diarrhoea in Calves, Piglets and Lambs", Journal of General Microbiology, vol. 129, p. 2659-2675, 1983.

Williams Smith, H., et al., The Control of Experimental *Escherichia coli* Diarrhoea in Calves by Means of Bacteriophages, Journal of General Microbiology, vol. 133, p. 1111-1126, 1987.

Soothill, J. S., et al., "The Efficacy of Phages in the Prevention of the Destruction of Pig Skin in vitro by *Pseudomonas aeruginosa*", Med. Sci. Res., vol. 16, p. 1287-1288, 1988.

Gachechiladze, K. K., et al., "Host-Controlled Modification and Restriction as a Criterion of Evaluating the Therapeutical Potential of Pseudomonas Phage", *J. Basic Microbiol.*, vol. 31, p. 101-106, 1991.

Adamia, Revaz S., et al., "The Virulent Bacteriophage IRA of *Salmonella typhimurium*: Cloning of Phage Genes which are Potentially Lethal for the Host Cell", *J Basic Microbiol.*, vol. 30, p. 707-716, 1990.

Karin E. Byers et al., "Disinfection of Hospital Rooms Contaminated with Vancomyci-Resistant *Enterococcus faecum*", Infection Control and Hospital Epidemiology, vol. 19, issue 4, p. 261-264, Apr. 1988.

Alavidze, Z., et al., "Isolation of Specific Lytic Phases Against Multidrug Resistant *Pseudomonas aeruginosa,*", American Soceity for Microbiology, Final Program (1999).

Kudva, Indira T., et al., "Biocontrol of *Escherichia coli* O157 with O157-Specific Bacteriophages," Applied and Environmental Microbiology, 65:3767-3773 (1999).

Lenski, Richard E., "Dynamics of Interactions Between Bacteria and Virulent Bacteriphage," *Adv. Microb. Ecol.*, 10:1-44 (1988).

Levin, Bruce R., et al., "Phage Therapy Revisited: The Population Biology of a Bacterial Infection and its Treatment with Bacteriophage and Antibiotics," The American Naturalist, 147:881-898 (1996).

Ochs, Hans D., "Immunologic Responses to Bacteriophage φX 174 in Immunodeficiency Disease," The Journal of Clinical Investigation, 50:2559-2567 (1971).

Slopek et al., "Results of Bacteriophage Treatment of Suppurative Bacterial Infections; I. General Evaluation of the Results," Arch. Immunol. Therapiae Exper., 31:267-291 (1983).

Slopek et al., "Results of Bacteriophage Treatment of Suppurative Bacterial Infections; II. Detailed Evaluation of the Results," Arch. Immunol. Therapiae Exper., 31:293-327 (1981).

Slopek et al., "Results of Bacteriophage Treatment of Suppurative Bacterial Infections; III. Detailed Evaluation of the Results Obtained in Further 150 Cases," *Arch. Immunol. Therapiae Exper.*, 32:317-335 (1984).

Slopek et al., "Results of Bacteriophage Treatment of Suppurative Bacterial Infections; IV. Evaluation of the Results Obtained in 370 Cases," *Arch. Immunol. Therapiae Exper.*, 33:219-240 (1985).

Slopek et al., "Results of Bacteriophage Treatment of Suppurative Bacterial Infections; V. Evaluation of the Results Obtained I Children," *Arch. Immunol. Therapiae Exper.*, 33:241-260 (1985).

Slopek et al., "Results of Bacteriophage Treatment of Suppurative Bacterial Infections; VI. Analysis of Treatment of Suppurative Staphylococcal Infections," *Arch. Immunol. Therapiae Exper.*, 33:261-275 (1985).

Slopek et al., "Results of Bacteriophage Treatment of Suppurative Bacterial Infections in the Years 1981-1986," *Arch. Immunol. Therapiae Exper.*, 35:569-584 (1987).

Soothill, J.S., "Bacteriophage Prevents Destruction of Skin Grafts by *Pseudomonas aeruginosa*," Burns, 20:209-211 (1994).

Soothill, J.S., "Treatment of Experimental Infections of Mice with Bacteriophages," *J. Med. Microbiol.*, 37:258-261 (1992).

Alavidze, A., et al, "Isolation of Specific Lytic Phages Against Multidrug Resistant *Pseudomonas aeruginosa*," The American Society for Microbiology, 99:447 (1999(.

Slopek, S., et al., "Results of Bacteriophage Treatment of Suppurative Bacterial Infections VI. Analysis of Treatment of Suppurative Staphylococcal Infections," Database Biosis 'Online, Biosciences Information Service, (1985).

Bogovazova, G.G., et al., "Immunobiological Properties & Therapeutic Effectiveness of Preparations from Klebsiella Bacteriophages," Zh. Mikrobiol. Epidemiol. Immunobiol., 3:30-33 (1992).

Barrow, P.A., "Bacteriophages Mediating Somatic Antigenic Conversion in *Salmonella cholerae-suis*: their Isolation from Sewage and Other *Salmonella* Serotypes Possessing the Somatic 6 Antigen," *Journal of General Microbiology*, 132:835-837 (1986).

Barrow, et al., "Salmonellosis—Prospects for Microbiology Control in Poultry," *Avian pathology*, 18:557-561 (1989).

Barrow, Paul A., et al., "Bacteriophage Therapy and Prophylaxis: Rediscovery and Renewed Assessment of Potential," *Trends in Microbiology*, 5:268-271 (1997).

Berchieri, A., Jr., et al., The Activity in the Chicken Alimentary Tract of Bacteriophages Lytic for *Salmonella typhimurium, Res. Microbiol.*, 142:541-549 (1991).

Williams Smith, H., et al., "Successful Treatment of Experimental *Escherichia coli* Infections in Mice Using Phage: Its General Superiority Over Antibiotics," *Journal of General Micorbiology*, 128:307-318 (1982).

Williams Smith, H., et al., "Effectiveness of Phages in Treating Experimental *Escherichia coli* Diarrhoea in Calves, Piglets and Lambs," *Journal of General Microbiology*, 129:2659-2675 (1983).

Williams Smith, H., et al., "The Control of Experimental *Escherichia coli* Diarrhoea in Calves by Means of Bacteriophages," *Journal of General Microbiology*, 133:1111-1126 (1987).

Soothill, J.S., et al., "The Efficacy of Phages in the Prevention of the Destruction of Pig Skin in vitro by *Pseudomonas aeruginosa*," *Med. Sci. Res.*, 16:1287-1288 (1988).

Gachechiladze, K.K., et al., "Host-Controlled Modification and Restriction as a Criterion of Evaluating the Therapeutical Potential of *Pseudomonas* Phage," *J. Basic Microbiol.*, 31:101-106 (1991).

Adamia, Revaz S., et al., "The Virulent Bacteriophage IRA of *Salmonella typhimurium*: Cloning of Phage Genes Which are Potentially Lethal for the Host Cell," *J. Basic Microbiol.*, 30:707-716 (1990).

\* cited by examiner

REDUCTION IN BACTERIAL COLONIZATION BY ADMINISTERING BACTERIOPHAGE COMPOSITIONS

RELATED APPLICATIONS

This application is a Continuation of U.S. patent application Ser. No. 09/757,685, filed Jan. 11, 2001. This present application claims priority to U.S. Provisional Patent Application No. 60/175,377 filed on Jan. 11, 2000; U.S. Provisional Patent Application No. 60/175,415 filed Jan. 11, 2000, Unites States Provisional Patent Application No. 60/175,416 filed Jan. 11, 2002; and U.S. Provisional Application No. 60/205, 240 filed May 19, 2000. The contents of these provisional applications are incorporated herein by reference in their entirety.

BACKGROUND OF THE INVENTION

1. Field of the Invention

The present invention is directed to the field of medical treatment and prevention of infections diseases; in particular, use of therapeutic compositions containing bacteriophage to reduce or eliminate colonization with potentially pathogenic bacteria (including bacterial strains resistant to many or most commonly used antimicrobial agents), thereby reducing the risk of subsequent disease occurrence.

2. Description of Related Art

Vancomycin-Resistant *Enterococcus*

Over the last ten years there has been an emergence of bacterial pathogens, which demonstrate resistance to many, if not all antimicrobial agents. This is particularly relevant in the institutional environment where nosocomial pathogens are under selective pressure due to extensive antimicrobial usage. A particular problem in this regard has been vancomycin-resistant enterococci (VRE), which are not treatable with standard classes of antibiotics. Despite the recent release of two drugs to which VRE are susceptible (quinupristin/dalfopristin and linezolid [Plouffe J F, Emerging therapies for serious gram-positive bacterial infections: A focus on linezolid. Clin Infect dis 2000 Suppl 4:S144-9), these microorganisms remain an important cause of morbidity and mortality in immunocompromised patients.

Enterococci are grain positive facultatively anaerobic cocci found in a variety of environmental sources including soil, food and water. They are also a common colonizing bacterial species in the human intestinal tract (i.e., the intestinal tract serves as a reservoir for the microorganism). Although the taxonomy of enterococci has not been finalized, it is generally accepted that the genus consists of 19 species.

Antibiotic management of serious enterococcal infections has always been difficult due to the intrinsic resistance of the organisms to most antimicrobial agents [Arden, R. C, and B. E. Murray, 1994, "*Enterococcus*: Antimicrobial resistance." In: Principles and Practice of Infectious Diseases Update, volume 2, number 4 (February, 1994). New York: Churchill Livingstone, Inc. 15 pps; Landman, D., and J. M. Quale, 1997, "Management of infections due to resistant enterococci: a review of therapeutic options." *J. Antimicrob. Chemother.*, 40:161-70; Moellering, R. C., 1998, "Vancomcyin-resistant enterococci." *Clin. Infect. Dis.* 26:1196-9]. In the 1970's enterococcal infections were treated with the synergistic combination of a cell wall active agent such as penicillin and are aminoglycoside (Moellering, et al. (1971), "Synergy of penicillin and gentamicin against enterococci." *J Infect. Dis.*, 124:S207-9; Standiford, et al. (1970), "Antibiotic synergism of enterococci: relation to inhibitory concentrations." *Arch. Intern: Med.*, 126: 255-9). However, during the 1980's enterococcal strains with high levels of aminoglycoside resistance and resistance to penicillin, mediated both by a plasmid-encoded β-lactamase and by changes in penicillin binding proteins, appeared (Mederski-Samoraj, et al. (1983), "High level resistance to gentamicin in clinical isolates of enterococci." *J. Infect. Dis.*, 147:751-7; Uttley, et al. (1988), "Vancomycin resistant enterococci." Lancet i:57-8). In 1988 the first VRE isolates were identified (Leclercq, et al. (1988), "Plasmid mediated resistance to vancomycin and teicoplanin in *Enterococcus faecium.*" *N Engl. J: Med.*, 319:157-61). Such organisms, called VRE because of resistance to vancomycin, are also resistant to the penicillin-aminoglyroside combination. VRE includes strains of several different enterococcal species with clinically significant VRE infections caused by *Enterococcus faecium* and *Enterococcus faecalis*.

Enterococci can cause a variety of infections including wound infection, endocarditis, urinary tract infection and bacteremia. After *Staphylococcus aureus* and coagulase negative staphylococci, enterococci are the most common cause of nosocomial bacteremia. Among immunocompromised patients, intestinal colonization with VRE frequently precedes, and serves as a risk factor for, subsequent VRE bacteremia (Edmond, et al. (1995), "Vancomycin resistant *Enterococcus faecium* bacteremia: Risk factors for infection." *Clin. Inf. Dis.*, 20:1126-33; Tornieporth, N. G., R. B. Roberts, J. John, A. Hafner, and L. W. Riley, 1996, "Risk factors associated with vancomycin-resistant *Enterococcus faecium* infection or colonization in 145 matched case patients and control patients." *Clin. Infect. Dis.*, 23:767-72.]. By using pulse field gel electrophoresis as a molecular typing tool investigators at the University of Maryland at Baltimore and the Baltimore VA Medical Center have shown VRE strains causing bacteremia in cancer patients are almost always identical to those which colonize the patients gastrointestinal tract (Roghmann M C, Qaiyumi S, Johnson J A, Schwalbe R, Morris J G (1997), "*Recurrent vancomycin-resistant Enterococcus faecium bacteremia in a leukemia patient who was persistently colonized with vancomycin-resistant enterococci for two years*." Clin Infect Dis 24:514-5). The risk of acquiring VRE increases significantly when there is a high rate of VRE colonization among patients on a hospital ward or unit (i.e., when there is high "colonization pressure"). In one study in the Netherlands, colonization pressure was the most important variable affecting acquisition of VRE among patients in an intensive care unit (Bonten M J, et al, "The role of "colonization pressure" in the spread of vancomycin-resistant enterococci: an important infection control variable." Arch Intern Med 1998; 25:1127-32). Use of antibiotics has been clearly shown to increase the density, or level of colonization, in an individual patient (Donskey C J et al, "Effects of antibiotic therapy on the density of vancomycin-resistant enterococci in the stool of colonized patients." N Engl J Med 2000; 343:1925-32): this, in turn, would appear to increase the risk of subsequent infection, and the risk of transmission of the organism to other patients.

Multi-Drug Resistant *Staphylococcus aureus* (MDRSA)

*S. aureus* is responsible for a variety of diseases ranging from minor skin infections to life-threatening systemic infections, including endocarditis and sepsis [Lowy, F. D., 1998, "*Staphylococcus aureus* infections." *N. Engl. J. Med,* 8:520-532]. It is a common cause of community- and nosocomially-acquired septicemia (e.g., of approximately 2 million infections nosocomially acquired annually in the United States, approximately 260,000 are associated with *S. aureus* [Emori, T. G., and R. P. Gaynes, 1993, "An overview of nosocomial infections, including the role of the microbiology laboratory," *Clin. Microbiol. Rev.,* 4:428-442]). Also, approximately 20% of the human population is stably colonized with *S. aureus,* and up to 50% of the population is transiently colonized, with diabetics, intravenous drug users, patients on dialysis, and patients with AIDS having the highest rates of *S. aureus* colonization [Tenover, F. C., and R. P. Gaynes, 2000, "The epidemiology of *Staphylococcus* infections," p. 414-421, In: V. A. Fischetti, R. P. Novick, J. J. Ferretti, D. A. Portnoy, and J. I. Rood (ed), *Gram-positive pathogens*, American Society for Microbiology, Washington, D.C.]. The organism is responsible for approximately one-half of all skin and connective tissue infections, including folliculitis, cellulitis, furuncules, and pyomyositis, and is one of the most common causes of surgical site infections. The mortality rate for *S. aureus* septicemia ranges from 11 to 48% [Mortara, L. A., and A. S. Bayer, 1993, "*Staphylococcus aureus* bacteremia and endocarditis. New diagnostic and therapeutic concepts." *Infect. Dis. Clin. North. Am.,* 1:53-68].

Methicillin was one of the first synthetic antibiotics developed to treat penicillin-resistant staphylococcal infections. However, the prevalence of methicillin-resistant *S. aureus* strains or "MRSA" (which also are resistant to oxacillin and nafcillin) has drastically increased in the United States and abroad [Panlilio, A. L., D. H. Culver, R. P. Gaynes, S. Banerjee, T. S. Henderson, J. S. Tolson, and W. J. Martone, 1992, "Methicillin-resistant *Staphylococcus aureus* in U.S. hospitals, 1975-1991." *Infect. Control Hosp. Epidemiol.,* 10:582-586]. For example, according to the National Nosocomial Infections Surveillance System [National Nosocomial Infections Surveillance (NNIS) report, data summary from October 1986-April 1996, issued May 1996, "A report from the National Nosocomial Infections Surveillance (NNIS) System." *Am. J. Infect. Control.,* 5:380-388], approximately 29% of 50,574 *S. aureus* nosocomial infections from 1987 to 1997 were resistant to the β-lactam antibiotics (e.g., oxacillin, nafcillin, methicillin), and the percent of MRSA strains among U.S. hospitals reached approximately 40% by the end of the same period. At the University of Maryland Medical Center, >50% of all *S. aureus* blood isolates are now methicillin resistant.

In this setting, there is great concern about the possible emergence of methicillin-resistant/multi-drug resistant *S. aureus* strains which are vancomycin resistant—and which would be essentially untreatable. Although overt resistance to vancomycin has not yet been documented in clinical isolates, there have been several reports of clinical infections with *S. aureus* strains having intermediate resistance to vancomycin (MICs=8 μg/ml), which suggests that untreatable staphylococcal infections may not be too far away [Tenover, F. C., and R. P. Gaynes. 2000]. Given the virulence of *S. aureus*, the emergence of such untreatable strains would be devastating and have a major impact on the way in which medicine is practiced in this country.

Staphylococcal species, including MDRSA, are common colonizers of the human nose; in one community-based study, 35% of children and 28% of their guardians had nasal *Staphylococcus aureus* colonization (Shopsin B, et al, "Prevalence of methicillin-resistant and methicillin-susceptible *Staphylococcus aureus* in the community." J Infect Dis 2000; 182:359-62.). Persons who are nasally colonized with MRSA have an increased risk of developing serious systemic infections with this microorganism, and, in particular, colonization or prior infection with MDRSA significantly increases the risk of subsequent bacteremia with MDRSA (Roghmann M C, "Predicting methicillin resistance and the effect of inadequate empiric therapy on survival in patients with *Staphylococcus aureus* bacteremia. Arch Intern Med 2000; 160:1001-4). As seen with VRE, the rate of colonization of persons with MDRSA on a unit (the colonization pressure) significantly increases the risk of acquisition of MDRSA for other patients on the unit (Merrer J. et al, ""Colonization pressure" and risk of acquisition of methicillin-resistant *Staphylococcus aureus* in a medical intensive care unit." Infect Control Hosp Epidemiol 2000; 21:718-23).

Multi-Drug Resistant *Pseudomonas aeruginosa*

*Pseudomonas aeruginosa* is a highly virulent gram-negative bacterial species that is responsible for bacteremia, wound infections, pneumonia, and urinary tract infections. Increasing problems with multi-antibiotic resistance in *Pseudomonas* has been noted in hospitals, with particular concern focusing on strains which are generally designated as "Imipenem-resistant *Pseudomonas*", reflecting the last major antimicrobial agent to which they have become resistant. Many of these strains are resistant to all major antibiotic classes, presenting substantive difficulties in management of infected patients.

As seen with other Gram-negative microorganisms, *Pseudomonas* strains often emerge as the primary colonizing flora of the posterior pharynx during hospitalization. Strains present in the posterior pharynx, in turn, are more likely to be aspirated into the lungs, and cause pneumonia. In this setting, colonization with multi-drug resistant *Pseudomonas* represents a potentially serious risk factor for development of multi-drug resistant *Pseudomonas* pneumonia.

Bacteriophage

Bacteriophage has been used therapeutically for much of this century. Bacteriophage, which derive their name from the Greek word "phago" meaning "to eat" or "bacteria eaters", were independently discovered by Twort and independently by D'Herelle in the first part of the twentieth century. Early enthusiasm led to their use as both prophylaxis and therapy for diseases caused by bacteria. However the results from early studies to evaluate bacteriophage as antimicrobial agents were variable due to the uncontrolled study design and the inability to standardize reagents. Later in well designed and controlled studies it was concluded that bacteriophage were not useful as antimicrobial agents (Pyle, N. J. (1936), *J. Bacteriol.,* 12:245-61; Colvin, M. G. (1932), *J. Infect Dis.,* 51:17-29; Boyd et al. (1944), *Trans R. Soc. Trop. Med. Hyg.,* 37:243-62).

This initial failure of phage as antibacterial agents may have been due to the failure to select for phage that demonstrated high in vitro lytic activity prior to in vivo use. For example, the phage employed may have had little or no activity against the target pathogen, were used against bacteria that were resistant due to lysogenization or the phage itself might be lysogenic for the target bacterium (Barrow, et al. (1997), "Bacteriophage therapy and prophylaxis: rediscovery and renewed assessment of potential." *Trends in Microbiology,* 5:268-71). However, with a better understanding of the phage-bacterium interaction and of bacterial virulence factors, it was possible to conduct studies which demonstrated the in vivo anti-bacterial activity of the bacteriophage (Asheshov, et al. (1937), *Lancet,* 1:319-20; Ward, W. E. (1943), *J. Infect. Dis.,* 72:172-6; Lowbury, et al. (1953), *J. Gen. Microbiol.,* 9:524-35). In the U.S. during the 1940's Eli Lilly commercially manufactured six phage products for human use including preparations targeted towards staphylococci, streptococci and other respiratory pathogens.

With the advent of antibiotics, the therapeutic use of phage gradually fell out of favor in the U.S. and Western Europe and little subsequent research was conducted. However, in the 1970's and 1980's there were reports of bacteriophage therapy continuing to be utilized in Eastern Europe, most notably in Poland and the former Soviet Union.

Phage therapy has been used in the former Soviet Union and Eastern Europe for over half a century, with research and production centered at the Eliava Institute of Bacteriophage in Tbilisi, in what is now the Republic of Georgia. The international literature contains several hundred reports on phage therapy, with the majority of the publications coming from researchers in the former Soviet Union and eastern European countries. To give but a few examples, phages have been reported to be effective in treating (i) skin and blood infections caused by *Pseudomonas, Staphylococcus, Klebsiella, Proteus*, and *E. coli* [Cislo, M., M. Dabrowski, B. Weber-Dabrowska, and A. Woyton, 1987, "Bacteriophage treatment of suppurative skin infections," 35(2):175-183; Slopek, S., I. Durlakowa, B. Weber-Dabrowska, A. Kucharewicz-Krukowska, M. Dabrowski, and R. Bisikiewicz, 1983, "Results of bacrteriophage treatment of suppurative bacterial infections. I. General evaluation of the results," *Archivum. Immunol. Therapiae Experimental*, 31:267-291; Slopek, S., B. Weber-Dabrowska, M. Dabrowski, and A. Kucharewicz-Krukowska, 1987, "Results of bacteriophage treatment of suppurative bacterial infections in the years 1981-1986,", 35:569-83], (ii) staphylococcal lung and pleural infections [Meladze, G. D., M. G. Mebuke, N. S. Chkhetia, N. I. Kiknadze, G. G. Koguashvili, I. I. Timoshuk, N. G. Larionova, and G. K. Vasadze, 1982, "The efficacy of Staphylococcal bacteriophage in treatment of purulent diseases of lungs and pleura," *Grudnaya Khirurgia*, 1:53-56 (in Russian, summary in English)], (iii) *P. aeruginosa* infections in cystic fibrosis patients [Shabalova, I. A., N. I. Karpanov, V. N. Krylov, T. O. Sharibjanova, and V. Z. Akhverdijan. "*Pseudomonas aeruginosa* bacteriophage in treatment of *P. aeruginosa* infection in cystic fibrosis patients," abstr. 443. In Proceedings of IX international cystic fibrosis congress, Dublin, Ireland], (iv) neonatal sepsis [Pavlenishvili, I., and T. Tsertsvadze. 1985. "Bacteriophage therapy and enterosorbtion in treatment of sepsis of newbornes caused by gram-negative bacteria." In abstracts, p. 104, Prenatal and Neonathal Infections, Toronto, Canada], and (v) surgical wound infections [Peremitina, L. D., E. A. Berillo, and A. G. Khvoles, 1981, "Experience in the therapeutic use of bacteriophage preparations in supportive surgical infections." *Zh. Mikrobiol. Epidemiol. Immunobiol.* 9:109-110 (in Russian)]. Several reviews of the therapeutic use of phages were published during the 1930s-40s [Eaton, M. D., and S. Bayne-Jones, 1934, "Bacteriophage therapy: review of the principles and results of the use of bacteriophage in the treatment of infections," *J. Am. Med. Assoc.*, p. 103; Krueger, A. P., and E. J. Scribner, 1941, "The bacteriophage: its nature and its therapeutic use," *J. Am. Med. Assoc.*, p. 116] and recently [Barrow, P. A., and J. S. Soothill, 1997, "Bacteriophage therapy and propylaxis—rediscovery and renewed assessment of potential," *Trends in Microbiol.*, 5(7):268-271; Lederberg, J., 1996, "Smaller fleas . . . ad infinitum: therapeutic bacteriophage," *Proc. Natl. Acad. Sci. USA*, 93:3167-3168]. In a recent paper published in the Journal of Infection (Alisky, J., K. Iczkowski, A. Rapoport, and N. Troitsky, 1998, "Bacteriophages show promise as antimicrobial agents," *J. Infect.*, 36:5-15), the authors reviewed Medline citations (published during 1966-1996) of the therapeutic use of phages in humans. There were twenty-seven papers from Britain, the U.S.A., Poland and the Soviet Union, and they found that the overall reported success rate for phage therapy was in the range of 80-95%.

These are several British studies describing controlled trials of bacteriophage raised against specific pathogens in experimentally infected animal models such as mice and guinea pigs (See, e.g., Smith. H. W., and M. B. Huggins "Successful treatment of experimental *Escherichia coli* infections in mice using phages: its general superiority over antibiotics" *J. Gen. Microbial.*, 128:307-318 (1982); Smith, H. W., and M. B. Huggins "Effectiveness of phages in treating experimental *E. coli* diarrhea in calves, piglets and lambs" *J. Gen. Microbiol.*, 129:2659-2675 (1983); Smith, H. W. and R. B. Huggins "The control of experimental *E. coli* diarrhea in calves by means of bacteriophage". *J. Gen. Microbial.*, 133: 1111-1126 (1987); Smith, H. W., R. B. Huggins and K. M. Shaw "Factors influencing the survival and multiplication of bacteriophages in calves and in their environment" *J. Gen. Microbial.*, 133:1127-1135 (1987)). These trials measured objective criteria such as survival rates. Efficacy against *Staphylococcus, Pseudomonas* and *Acinetobacter* infections were observed. These studies are described in more detail below.

One U.S. study concentrated on improving bioavailability of phage in live animals (Merril, C. R., B. Biswas, R. Carlton, N. C. Jensen, G. J. Greed, S. Zullo, S. Adhya "Long-circulating bacteriophage as antibacterial agents" *Proc. Natl. Acad Sci. USA*, 93:3188-3192 (1996)). Reports from the U.S. relating to bacteriophage administration for diagnostic purposes have indicated phage have been safely administered to humans in order to monitor humoral immune response in adenosine deaminase deficient patients (Ochs, et al. (1992), "Antibody responses to bacteriophage phi X174 in patients with adenosine deaminase deficiency." *Blood,* 80:1163-71) and for analyzing the importance of cell associated molecules in modulating the immune response in humans (Ochs, et al. (1993), "Regulation of antibody responses: the role of complement acrd adhesion molecules." *Clin. Immunol. Immunopathol.,* 67:S33-40).

Additionally, Polish, Georgian, and Russian papers describe experiments where phage was administered systemically, topically or orally to treat a wide variety of antimicrobial resistant pathogens (See, e.g., Shabalova, I. A., N. I. Karpanov, V. N. Krylov, T. O. Sharibjanova, and V. Z. Akhverdijan. "*Pseudomonas aeruginosa* bacteriophage in treatment of *P. aeruginosa* infection in cystic fibrosis patients," Abstr. 443. In Proceedings of IX International Cystic Fibrosis Congress, Dublin, Ireland; Slopek, S., I. Durlakowa, B. Weber-Dabrowska, A. Kucharewicz-Krukowska, M. Dabrowski, and R Bisikiewicz. 1983. "Results of bacteriophage treatment of suppurative bacterial infections. I. General evaluation of the results." *Archivum, Immunol. Therapiae Experimental*, 31:267-291; Slopek, S., B. Weber-Dabrowska, M. Dabrowski, and A. Kucharewicz-Krukowska. 1987. "Results of bacteriophage treatment of suppurative bacterial infections in the years 1981-1986", *Archivum Immunol. Therapiae Experimental,* 35:569-83.

Infections treated with bacteriophage included osteomyelitis, sepsis, empyema, gastroenteritis, suppurative wound infection, pneumonia and dermatitis. Pathogens involved included *Staphylococci, Streptococci, Klebsiella, Shigella, Salmonella, Pseudomonas, Proteus* and *Escherichia*. These articles reported a range of success rates for phage therapy between 80-95% with only rare reversible allergic or gastrointestinal side effects. These results indicate that bacteriophage may be a useful adjunct in the fight against bacterial diseases. However, this literature does not describe, in any way anticipate, or otherwise suggest the use of bacteriophage to modify the composition of colonizing bacterial flora in humans, thereby reducing the risk of subsequent development of active infections.

SUMMARY OF THE INVENTION

According to one embodiment of the present invention, a lytic bacteriophage which infects *Enterococcus*, wherein no more than 30% of the *Enterococcus* strains in a collection of more than 100 genetically diverse vancomycin resistant *Enterococcus* (VRE) strains are resistant to infection by said bacteriophage is disclosed. The bacteriophage may produces lytic infection in at least 200 genetically diverse VRE isolates. The bacteriophage preparation may be administered orally to patients who are colonized with VRE who are admitted to a medical facility. These patients may include, inter alia, leukemia patients, lymphoma patient, transplant patients and AIDS patients. The bacteriophage may also be administered to all patients admitted at the medical facility. Administration of this bacteriophage will reduce or eliminate colonization with VRE, thereby reducing the risk that these patients will subsequently develop serious systemic infections with this highly resistant microorganism. Reduction or elimination of colonization will also decrease the VRE "colonization pressure" in the hospital or specific units of the hospital, thereby reducing the risk that VRE will be acquired by persons who currently are neither colonized or infected with the pathogen.

In one embodiment, the present invention provides a method for reducing the risk of bacterial infection or sepsis in a susceptible patient by treating the susceptible patient with a pharmaceutical composition containing bacteriophage of one or more strains which produce lytic infections in pathogenic bacteria. Preferably, treatment of the patient reduces the level of colonization with pathogenic bacteria susceptible to the bacteriophage by at least one log. In a typical embodiment, the susceptible patient is an immunocompromised patient selected from the group consisting of leukemia patients, lymphoma patients, carcinoma patients, sarcoma patients, allogeneic transplant patients, congenital or acquired immunodeficiency patients, cystic fibrosis patients, and AIDS patients. In a preferred mode, the patients treated by this method are colonized with the pathogenic bacteria subject to infection by said bacteriophage.

In a preferred embodiment of this invention, the risk of infection is reduced by administering a composition comprising bacteriophage which produce lytic infections in pathogenic bacteria selected from vancomycin-resistant *enterococcus* (VRE), pneumococcal species, methicillin-resistant *Staphylococcus aureus*, multi-drug resistant *Staphylococcus aureus* (MDRSA), multi-drug resistant *Pseudomonas* species, *Nesseria* sp., *Hemophilus* sp., *Proteus* sp., *Klebsiella* sp. and *Esherichia coli*. Preferably, the pathogenic bacteria are selected from VRE, MDSA, and multi-drug resistant *Pseudomonas*. In a preferred embodiment of this invention, the bacteriophage composition is in a form selected from a parenteral composition, an oral tablet, capsule or liquid, a nasal aerosol, a throat wash, a toothpaste, and a topical ointment. Preferably, the pharmaceutical composition contains a plurality of bacteriophage strains. More preferably, the pharmaceutical composition contains bacteriophage strains which produce lytic infections in pathogenic bacteria of a plurality of bacterial strains or bacteriophage strains which produce lytic infections in pathogenic bacteria of a plurality of bacterial species.

In a preferred embodiment, the present invention provides a method for reducing the risk of bacterial infection or sepsis in a patient having a wound selected from an ulcer, a laceration, a deep penetrating wound and a surgical wound by treating the patient with a pharmaceutical composition containing bacteriophage of one or more strains which produce lytic infections in pathogenic bacteria capable of infecting these wounds. Preferably, the composition is a topical ointment, an irrigation solution or a component of a wound dressing.

In another embodiment, this invention provides a method for reducing the incidence of infection by selected bacteria in a medical facility by administering to patients who are admitted to said medical facility a bacteriophage preparation which reduces the colonization level by the selected bacteria in patients at risk for infection by the selected bacteria. In a typical embodiment, the patients at risk for infection are selected from the group consisting of leukemia patients, lymphoma patients, carcinoma patients, sarcoma patients, allogeneic transplant patients, congenital or acquired immunodeficiency patients, cystic fibrosis patients, and AIDS patients. In another embodiment, the bacteriophage preparation is administered to substantially all patients admitted to said medical facility. In a preferred embodiment, the bacteriophage preparation is administered to substantially all patients colonized with the selected bacteria who are admitted to said medical facility. In another preferred embodiment, the selected bacteria is VRE, MDRSA, or multi-drug resistant *Pseudomonas*.

According to another embodiment of the present invention, a bacteriophage preparation which reduces the number of VRE in experimentally infected mice by at least 1 log is disclosed.

According to another embodiment of the present invention, a lytic bacteriophage which infects *Staphylococcus aureus*, wherein no more than 30% of the Staphylococcal strains in a collection of more than 100 genetically diverse multi-drug resistant *Staphylococcus aureus* (MDRSA) strains are resistant to infection by said bacteriophage is disclosed. The bacteriophage may produces lytic infection in at least 200 genetically diverse MDRSA isolates. The bacteriophage preparation may be administered via nasal spray to individuals who are nasally colonized with MDRSA, particularly to a subpopulation made up of all such individuals who are admitted to a medical facility. The bacteriophage may also be administered to all patients admitted at the medical facility. Administration of this bacteriophage will reduce or eliminate colonization with MDRSA, thereby reducing the risk that these patients will subsequently develop serious systemic infections with this highly resistant microorganism. Reduction or elimination of colonization will also decrease the MDRSA "colonization pressure" in the hospital or specific units of the hospital, thereby reducing the risk that MDRSA will be acquired by persons who currently are neither colonized or infected with the pathogen.

According to one embodiment of the present invention, a lytic bacteriophage which infects *Pseudomonas aeruginosa*, wherein no more than 30% of the *Pseudomonas* strains in a collection of more than 100 genetically diverse multi-antibiotic resistant *Pseudomonas aeruginosa* strains are resistant to infection by said bacteriophage is disclosed. The bacteriophage may produces lytic infection in at least 200 genetically diverse isolates. The bacteriophage preparation may be administered by mouth wash or gargle to individuals who are colonized with multi-drug resistant *Pseudomonas aeruginosa*, particularly to a subpopulation made up of all such individuals who are admitted to a medical facility. The bacteriophage may also be administered to all patients admitted at the medical facility. Administration of this bacteriophage will reduce or eliminate colonization with multi-drug resistant *Pseudomonas* strains, thereby reducing the risk that these patients will subsequently develop serious systemic infections with this highly resistant microorganism. This may also be expected to reduce the "colonization pressure" of this microorganism, thereby reducing the risk that it will be acquired by persons who are currently not colonized or infected.

DETAILED DESCRIPTION OF THE EMBODIMENTS

Bacteriophage technology can be of value in managing a large variety of bacterial infections because: (i) bacteriophages are highly specific and very effective in lysing targeted pathogenic bacteria, (ii) bacteriophages are absolutely specific for prokaryotes, and do not affect humans or animals, (iii) bacteriophages are safe, as underscored by their extensive clinical use in Eastern Europe and the former Soviet Union, and the commercial sale of phages in the 1940's in the United States, (iv) phage preparations can rapidly be modified to combat the emergence of newly arising bacterial threats, and (v) phage production is seen to be cost-effective for large-scale applications in a variety of medical settings. Of particular relevance, bacteriophage will not kill non-pathogenic, "normal flora" bacteria, thereby retaining the "colonization resistance" of reservoirs such as the human intestinal tract, the nose, and the posterior pharynx. Accordingly, the present invention envisions using lytic phages (in combination with antibiotics or alone) to prophylactically or therapeutically eliminate various bacteria capable of causing diseases of the gastrointestinal, genitourinary, and respiratory tracts, and skin, oral cavity, and bloodstream. In accordance with this invention, therapeutic phages can be administered in a number of ways, in various formulations, including: (i) orally, in tablets or liquids, (ii) locally, in tampons, rinses or creams, (iii) aerosols, and (iv) intravenously.

One benefit of bacteriophage therapy when compared to antibiotic therapy relates to the relative specificity of the two therapeutic modalities. Bacteriophage are specific for particular bacterial strains or species, while antibiotics typically are broadly effective against a large multiplicity of bacterial species or genera. It is well known that normal individuals are colonized with innocuous bacteria, and this colonization may be beneficial to the colonized individual (see U.S. Pat. No. 6,132,710, incorporated herein by reference). Antibiotic therapy can severely alter colonization or even eliminate beneficial colonization completely. This may have adverse effects, such as the outgrowth of opportunistic species such as *Clostridium difficile*, which then leads to an antibiotic-associated colitis. In contrast, bacteriophage therapy specifically affects the bacterial strains that are sensitive or susceptible to lytic infection by the particular bacteriophage in the therapeutic composition, but leaves other (innocuous or beneficial) bacteria unaffected. Thus, bacteriophage therapy is preferable for prophylactic treatment where alteration of normal microflora should be minimized.

In a preferred mode of this invention, phage technology is focused on two important human pathogens, VRE and MDRSA, and the value of VRE- and MDRSA-specific lytic phages in different settings: (i) oral administration of phages for prophylaxis against septicemia, (ii) local application of phages for prophylaxis/treatment of skin and wound infections, (iii) intravenous administration of phages for therapy of septicemia, and (iv) the use of aerosolized phages against respiratory pathogens.

VRE infection has become a particularly serious problem among immunocompromised and/or seriously ill patients in intensive care units, cancer centers and organ transplant units. Since VRE are resistant to all currently used antimicrobials, alternate approaches to reducing or eliminating VRE gastrointestinal colonization in immunocompromised patients must be found in order to reduce the prevalence of VRE bacteremia. Oral administration of lytic bacteriophage active against VRE is one such approach.

The general rule is that patients first become colonized by pathogenic bacteria present in their immediate environment before developing illness due to those bacteria. Serious VRE infections, including septicemia, usually are preceded by intestinal colonization with the infecting organisms; therefore, the risk of septicemia is likely to be decreased by reducing colonization prior to periods when patients are severely neutropenic or otherwise immunosuppressed (i.e., reducing intestinal colonization may also reduce the risk of bloodstream invasion). The present inventors have discovered that certain strains of bacteriophage are particularly effective at lysing VRE. By administering these VRE-active bacteriophage to persons colonized with VRE, it is possible to substantially reduce or even eliminate VRE from the colonized person. Thus, the present invention provides strains of phage which are particularly effective against VRE, methods for obtaining additional strains of VRE-active phage, methods for treating patients colonized with VRE by administering VRE-active phage, and methods of reducing nosicomial infection rate by administering VRE-active phage in vivo, ex vivo, or both, to selected locations, areas, objects and/or persons.

Analogous approaches using bacteriophage targeted to other pathogenic bacteria are also contemplated by this invention. *S. aureus* phage preparations can reduce contamination of skin and wounds with *S. aureus*, which in turn may prevent the development of serious surgical site infections and septicemia. Phage active against *Pseudomonas* species can be used to reduce colonization that threatens to develop into pneumonia in immunocompromised patients or in individuals suffering from cystic fibrosis.

Isolation of Bacteriophage

The present inventors have isolated several lytic phages active against genetically diverse (as assessed by pulsed field gel electrophoresis and/or arbitrary pruned polymerase chain reaction or other nucleic acid amplification techniques) VRE strains. In vitro susceptibility tests involving 234 VRE strains (184 *E. faecium*, 41 *E. faecalis* and 6 *E. gallinarium* isolated from patients at the University of Maryland and the Baltimore VA Medical Center, and 3 *E. faecium* ATCC strains), resulted in the Intralytix phage collection being able to cumulatively lyse all VRE strains in the collection, with one particular phage being able to lyse 95% of VRE strains. Furthermore mice whose gastrointestinal tract was colonized with VRE under selective pressure of antibiotic administration, were orogastrically administered VRE-active phages, which resulted in a 1 to 3 log reduction of VRE gastrointestinal colonization compared to a control group of animals not given phage. This occurred within a 48 to 72 hour time frame. No side effects due to the phage were observed.

Bacteriophage strains may be isolated by analogous procedures to those used to isolate the VRE-active strains described herein. Suitable bacteriophage may be isolated from any sample containing bacteriophage, which typically are found in association with their host bacteria. Thus, any source that might be expected to contain VRE is suitable for use as a source of VRE-active bacteriophage. Such samples include fecal, urine, or sputum samples from patients, particularly patients undergoing acute or prophylactic antibiotic therapy, patients in intensive care units or immunocompromised patients. Such patients may include but are not limited to burn patients, trauma patients, patients receiving bone marrow and/or organ transplants, cancer patients, patients with congenital or acquired immunodeficiency diseases, dialysis patients, liver disease patients, and patients with acute or chronic renal failure. Body fluids including ascites, pleural effusions, joint effusions, abscess fluids, and material obtained from wounds. While humans are the primary reservoir for VRE, the organism also can be readily found in the immediate environment of infected/colonized patients such as bedrails, bed sheets, furniture, etc. (Bodnar, U. R. et al (1996), "Use of in house studies of molecular epidemiology and full species identification of controlling spread of vancomycin resistant *Enterococcus faecalis* isolates", *J. Clin. Microbiol.*, 34: 2129-32; Bonten, M. J. M. et al (1996), "Epidemiology of colonization of patients and the environment with vancomycin resistant enterococci." *Lancet*, 348: 1615-19; Noskin, G. A. (1995), "Recovery of vancomycin resistant enterococci on fingertips and environmental surfaces." *Infect. Control Hosp. Epidemiol.*, 16: 577-81). Consequently, samples for bacteriophage isolation may also be obtained from nonpatient sources, including sewage, especially sewage streams near intensive care units or other hospital venues, or by swab in hospital areas associated with risk of nosicomial infection, such as intensive care units. Other suitable sampling sites include nursing homes, rest homes, military barracks, dormitories, classrooms, and medical waste facilities. Phages also can be isolated from rivers and lakes, wells, water tables, as well as other water sources (including salt water). Preferred sampling sites include water sources near likely sites of contamination listed above.

Suitable methods for isolating pure bacteriophage strains from a bacteriophage-containing sample are well known, and such methods may be adapted by the skilled artisan in view of the guidance provided herein. Isolation of VRE-active bacteriophage from suitable samples typically proceeds by mixing the sample with nutrient broth, inoculating the broth with a host bacterial strain, and incubating to enrich the mixture with bacteriophage that can infect the host strain. An *Enterococcus* sp. strain will be used as the host strain, preferably a VRE strain. After the incubation for enrichment, the mixture is filtered to remove bacterial leaving lytic bacteriophage in the filtrate. Serial dilutions of the filtrate are plated on a lawn of VRE, and VRE-active phage infect and lyse neighboring bacteria. However the agar limits the physical spread of the phage throughout the plate, resulting in small visibly clear areas called plaques on the plate where bacteriophage has destroyed VRE within the confluent lawn of VRE growth. Since one plaque with a distinct morphology represents one phage particle that replicated in VRE within that area of the bacterial lawn, the purity of a bacteriophage preparation can be ensured by removing the material in that plaque with a pasteur pipette (a "plaque pick") and using this material as the inoculum for further growth cycles of the phage. The bacteriophage produced in such cycles represent a single strain or "monophage." The purity of phage preparation (including confirmation that it is a monophage and not a polyvalent phage preparation) is assessed by a combination of electron microscopy, SDS-PAGE, DNA restriction digest and analytical ultracentrifugation. In addition, each phage is uniquely identified by its DNA restriction digest profile, protein composition, and/or genome sequence.

Individual VRE-active bacteriophage strains (i.e., monophages) are propagated as described for enrichment culture above, and then tested for activity against multiple VRE strains to select broad-spectrum VRE-active bacteriophage. Efforts are made to select phages that (i) are lytic, (ii) are specific to enterococci, (iii) lyse more than 70% of the VRE strains in our VRE strain collection, and/or (iv) lyse VRE strains resistant to other VRE phages previously identified. It is also possible to select appropriate phages based upon the sequences of DNA or RNA encoding proteins involved in the binding and/or entry of phage into their specific host, or based upon the amino acid sequences or antigenic properties of such proteins.

Quantities of broad-spectrum VRE-active bacteriophage needed for therapeutic uses described below may be produced by culture on a suitable host strain in the manner described above for enrichment culture. When performing an enrichment culture to produce bacteriophage for therapeutic use, a host strain is selected based on its ability to give a maximum yield of phage, as determined in pilot experiments with several different host VRE strains. If two or more host strains give similar yield, the strain most sensitive to antibiotics is selected.

The techniques described herein for isolation of VRE monophages are applicable to isolation of bacteriophages that are lytic for other pathogenic bacteria. It is within the skill in the art to substitute host strains of other bacteria in the methods described herein in order to isolate phage specific for those bacteria. Starting the phage isolation process with samples selected from environments that also contain bacteria of the host species will accelerate the process.

Patient Population

Any patient who is at risk for colonization with VRE or who has proven VRE colonization is a candidate for treatment according to the method of this invention. Intestinal colonization with VRE is relatively common in institutionalized patients undergoing antimicrobial therapy. In studies conducted in 1993-94, 17-19% of a random sample of all patients at the University of Maryland Hospital were colonized with VRE (Morris, et al. (1995), "Enterococci resistant to multiple antimicrobial agents including vancomycin." *Ann. Int. Med.*, 123:250-9), while in an identical study conducted in 1996 this increased to 23.8%. Once colonized with VRE, a patient may remain colonized for life; however once off antimicrobial therapy, VRE colonization may drop to levels not detectable in routine stool culture. Colonized persons though who also subsequently become immunocompromised are at risk for developing bacteremia (Edmond, et al., 1995; Tornieporth, et al (1996), "Risk factors associated with vancomycin resistant *Enterococcus faecium* colonization or infection in 145 matched case patients and control patients." *Clin. Infect. Dis.*, 23:767-72).

VRE infection is a particularly serious problem among immunocompromised and/or seriously ill patients in cancer centers, intensive care units, and organ transplant centers. In case control studies VRE has been linked to antimicrobial use and severity of illness (as measured by APACHE score) (Handwerger, et al. (1993), "Nosocomial outbreak due to *Enterococcus faecium*, highly resistant to vancomycin, penicillin and gentamicin." *Clin. Infect. Dis.*, 16:750-5; Montecalvo, et al. (1996), "Bloodstream infections with vancomycin resistant enterococci." *Arch. Intern. Med.*, 156:1458-62; Papanicolaou, et al. (1996), "Nosocomial infections with vancomycin-resistant *Enterococcus faecium* in liver transplant patients: Risk factors for acquisition and mortality." *Clan. Infect. Dis.*, 23:760-6; Roghmann, et al., (1997), "Recurrent vancomycin resistant *Enterococcus faecium* bacteremia in a leukemic patient who was persistently colonized with vancomycin resistant enterococci for two years." *Clin. Infect. Dis.*, 24; 514-5). Investigators at the University of Maryland at Baltimore and the Baltimore VA Medical Center have demonstrated by pulse field electrophoresis that VRE strains causing bacteremia in cancer patients are almost always identical to those that colonize the patient's gastrointestinal tract.

Three categories of immunocompromised patients subjected to prolonged antimicrobial administration in a institutionalized setting and who would be susceptible to VRE gastrointestinal colonization are: I) leukemia (30,200 patients per year in the U.S.) and lymphoma patients (64,000 patients per year in the U.S.), 2) transplant patients (20,961 per year in the U.S.), and 3) AIDS patients (66,659 patients per year in the U.S.). The total number of patients in the immunocompromised category is 181,800 per year in the U.S. Pfundstein, et al., found that the typical rate of enterococcal gastrointestinal colonization among renal and pancreas transplant patients receiving antibiotics in an institutional setting was 34% (38/102) with 4 (11%) of these isolates being VRE (Pfundstein, et al. (1999), "A randomized trial of surgical antimicrobial prophylaxis with and without vancomycin in organ transplant patients." Clin. Transplant., 13:245-52). Therefore the rate of gastrointestinal colonization by VRE in this immunocompromised population would be 0.34×0.11=0.04 or 4% of the total patient population. One can therefore estimate VRE gastrointestinal, colonization to be 181,800×0.04=7272 patients per year.

Formulation and Therapy

According to this invention, VRE-active bacteriophage are preferably formulated in pharmaceutical compositions containing the bacteriophage and a pharmaceutically acceptable carrier, and can be stored as a concentrated aqueous solution or lyophilized powder preparation. Bacteriophage may be formulated for oral administration by resuspending purified phage preparation in aqueous medium, such as deionized water, mineral water, 5% sucrose solution, glycerol, dextran, polyethylene glycol, sorbitol, or such other formulations that maintain phage viability, and are non-toxic to humans. The pharmaceutical composition may contain other components so long as the other components do not reduce the effectiveness (ineffectivity) of the bacteriophage so much that the therapy is negated. Pharmaceutically acceptable carriers are well known, and one skilled in the pharmaceutical art can easily select carriers suitable for particular routes of administration (Remington's Pharmaceutical Sciences, Mack Publishing Co., Easton, Pa., 1985).

The pharmaceutical compositions containing VRE-active bacteriophage may be administered by parenteral (subcutaneously, intramuscularly, intravenously, intraperitoneally, intrapleurally, intravesicularly or intrathecally), topical, oral, rectal, inhalation, ocular, otic, or nasal route, as necessitated by choice of drug and disease.

Injection of specific lytic phages directly into the bloodstream can eliminate or significantly reduce the number of targeted bacteria in the blood. If, after either oral or local administration, phages get into the bloodstream in sufficient numbers to eliminate bacteria from the bloodstream, septicemia may be treated by administering phages orally (or locally). If the phages do not get into the bloodstream in sufficient numbers to eliminate bacteria from the bloodstream, the utility of direct i.v. injection of phages for treating septic infections can be used to treat bloodstream infections caused by VRE and other pathogenic bacteria, and can provide an urgently needed means for dealing with currently untreatable septicemic infections.

Dose and duration of therapy will depend on a variety of factors, including the patient age, patient weight, and tolerance of the phage. Bacteriophage may be administered to patients in need of the therapy provided by this invention by oral administration. Based on previous human experience in Europe, a dose of phage between $10^7$ and $10^{11}$ PFU will be suitable in most instances. The phage may be administered orally in, for example, mineral water, optionally with 2.0 grams of sodium bicarbonate added to reduce stomach acidity. Alternatively, sodium bicarbonate may be administered separately to the patient just prior to dosing with the phage. Phages also may be incorporated in a tablet or capsule which will enable transfer of phages through the stomach with no reduction of phage viability due to gastric acidity, and release of fully active phages in the small intestine. The frequency of dosing will vary depending on how well the phage is tolerated by the patient and how effective a single versus multiple dose is at reducing VRE gastrointestinal colonization.

The dose of VRE-active bacteriophage and duration of therapy for a particular patient can be determined by the skilled clinician using standard pharmacological approaches in view of the above factors. The response to treatment may be monitored by, analysis of blood or body fluid levels of VRE, or VRE levels in relevant tissues or monitoring disease state in the patient. The skilled clinician will adjust the dose and duration of therapy based on the response to treatment revealed by these measurements.

One of the major concerns about the use of phages in clinical settings is the possible development of bacterial resistance against them. However, as with antimicrobial resistance, the development of resistance to phages takes time. The successful use of phages in clinical settings will require continual monitoring for the development of resistance, and, when resistance appears, the substitution of other phages to which the bacterial mutants are not resistant. In general, phage preparations may be constructed by mixing several separately grown and well-characterized lytic monophages, in order to (i) achieve the desired, broad target activity of the phage preparation, (ii) ensure that the preparation has stable lytic properties, and (iii) minimize the development of resistance against the preparation.

The development of neutralizing antibodies against a specific phage also is possible, especially after parenteral administration (it is less of a concern when phages are administered orally and/or locally). However, the development of neutralizing antibodies may not pose a significant obstacle in the proposed clinical settings, because the kinetics of phage action is much faster than is the host production of neutralizing antibodies. For VRE for example, phages will be used for just a few days, sufficient to reduce VRE colonization during the time period when immunocompromised patients are most susceptible to the development of potentially fatal VRE septicemia, but not long enough for phage-neutralizing antibodies to develop. If the development of antiphage antibodies is a problem, several strategies can be used to address this issue. For example, different phages having the same spectrum of activity (but a different antigenic profile) may be administered at different times during the course of therapy. On a more sophisticated level, therapeutic phages may be genetically engineered which will have a broad lytic range and/or be less immunogenic in humans and animals.

Environmental Therapy

In the 1980's a number of British studies were conducted which demonstrated the efficacy of bacteriophage prophylaxis and therapy in mice and farm animal models. These studies were significant because the titers of the phage preparations administered were significantly less than the bacterial inoculum indicating in vivo bacteriophage multiplication. For example, Smith et al (Smith, et al. (1982), "Successful treatment of experimental *Escherichia coli* infections in mice using phage: its general superiority over antibiotics." *J. Gen. Microbiol.*, 128:307-1825) found intramuscular inoculation of mice with $10^6$ CFU of *E. coli* with K1 capsule killed 10/10 mice. However when mice were simultaneously intramuscularly inoculated with $10^4$ PFU of phage, at a separate site, 10/10 mice survived. Smith and coworkers demonstrated that administration of a mixture of two phage resulted in high levels of protection of calves with diarrhea induced by *E. coli* with K 88 or K99 fimbriae (Smith, et al. (1983), "Effectiveness of phages in treating experimental *Escherichia coli* diarrhea in calves, piglets and lambs." *J. Gen. Microbiol.*, 129: 2659-75; Smith, et al. (1987), "The control of experimental *Escherichia coli* diarrhea in calves by means of bacteriophage." *J. Gen. Microbiol.*, 133:1111-26; Smith, et al. (1987), "Factors influencing the survival and multiplication of bacteriophages in calves and in their environment." *J. Gen. Microbiol.*, 133:1127-35). If the phage was administered before or at the same time as *E. coli* no deaths occurred and complete protection was attained. Control animals developed watery diarrhea and died within 2 to 5 days. If phage administration was delayed until the onset of diarrhea, protection was not complete although the severity of infection was greatly reduced and no deaths were observed. Berchieri, et al., found that fewer chicks orally infected with $10^9$ PFU of *Salmonella typhimurium* died when $10^9$ PFU of *Salmonella* specific phage was orally administered soon after initiation of the bacterial infection (Berchieri, et al. (1991), "The activity in the chicken alimentary tract of bacteriophages lytic for *Salmonella typhimurium.*" *Res. Microbiol*, 142:541-49). They also found that the phage was readily spread between the different infected birds.

Environmental applications of phage in health care institutions could lie most useful for equipment such as endoscopes and environments such as ICUs which maybe potential sources of nosocomial infection due to pathogens such as VRE but which may be difficult or impossible to disinfect. Phage would be particularly useful in treating equipment or environments inhabited by bacterial genera such as *Pseudomonas* which may become resistant to commonly used disinfectants. In the Soviet Union there has been a report that application of phage to the hospital environment has resulted in killing targeted bacteria such as *Staphylococci* and *Pseudomonas* within 48-72 hours. Phage persisted in the environment as long as there were target bacteria present and upon elimination of target bacteria, phage became undetectable in 6-8 days (Alavidze, et al, 1988, "Use of specific bacteriophage in the prophylaxis of intrahospital infections caused by *P. aeruginosa.*" in Abstracts., All-Soviet Union conference "Modern biology at the service of public health". Kiev, Ukraine).

Phage compositions used to disinfect inanimate objects or the environment may be sprayed, painted, or poured, onto such objects or surfaces in aqueous solutions with phage titers ranging between $10^7$-$10^{11}$ PFU/ml. Alternatively, phage may be applied by aerosolizing agents that might include dry dispersants which would facilitate distribution of the phage into the environment. Such agents may also be included in the spray if compatible with phage viability and nontoxic in nature. Finally, objects may be immersed in a solution containing phage. The optimal numbers and timing of applications of phage compositions remains to be determined and would be predicated by the exact usage of such products.

Since phage are normally widely present in the environment and are found even in food or drugs, there is minimal safety concern with regard to applying phage preparations to the environment.

As reported above, Smith and Huggins in England found that *E. coli* induced diarrhea in calves could be prevented by simply spraying the litter in the calf rooms with an aqueous phage preparation or even by keeping the calves in uncleaned rooms previously occupied by calves whose *E. coli* infections had been treated with phage. There is also data from the Soviet Union indicating the efficacy of phage to rid chicken houses of *Staphylococci* (Ponomarchuk, et al., (1987), "Strain phage *Staphylococci* applicable for prophylaxis and therapy of poultry *Staphylococcus.*" Soviet patent N1389287, Dec. 15, 1987).

In the future, application of VRE phage to the environment of farm animals such as chickens or cattle maybe necessary to reduce VRE in this setting if VRE become prevalent in such environments and such animal VRE are capable, upon being consumed in contaminated food, of transiently colonizing the human gastrointestinal tract long enough to transfer antibiotic resistance gene transposons to normal gut flora (Latta, S. (1999) "Debate heats up over antibiotic-resistant foodborne bacteria." *The Scientist* 13; (14) 4-5).

Alternatively, colonization in the farm animals may be reduced by administering bacteriophage to the animals (or treating the animals' environment) using phage that produce lytic infections in target bacteria which colonize the animals. Such unwanted colonization may be a particular problem with intensive agricultural techniques, such as those used for chickens or veal calves. Target organisms include *Salmonella* sp. and *E. coli* H7:0157.

Bacteriophage Cocktails

This invention also contemplates phage cocktails which may be custom tailored to the pathogens that are prevalent in a certain situation. Typically, pathogenic bacteria would be initially isolated from a particular source (e.g., a patient or location contaminated with VRE) and susceptibility testing of the pathogens to various bacteriophage strains would be performed, analogous to antimicrobial susceptibility testing. Once each pathogen's phage susceptibility profile is determined, the appropriate phage cocktail can be formulated from phage strains to which the pathogens are susceptible and administered to the patient. Since phage would often be used in institutional settings where pathogens are resistant to many antimicrobial agents, phage cocktails would often consist of phage lytic for the most prevalent institutional pathogens which, in addition to enterococci, are *Staphylococcus aureus*, *Staphylococcus epidermidis*, *E. coli* and *Pseudomonas aeruginosa*. Also since enterococci are often involved in polymicrobial infections along with other gastrointestinal commensals, such as in pelvic wound infections, the approach of therapeutically using cocktails of phage lytic against different bacterial species would be most appropriate. Since phage cocktails would be constructed of phage against institutional pathogens, isolation of such phage would be most successful from the sewage of such institutions. Typically, the phage cocktail will include one or more VRE-active bacteriophage according to this invention.

It may be appropriate to use certain phage cocktails in agricultural settings where there are certain human pathogens such as *Salmonella* and *Campylobacter* inherent to poultry or livestock and which contaminate the environment of such animals on an ongoing basis. The result is a continuing source of infection by such pathogens.

Bacteriophage cocktails may be applied contemporaneously—that is, they may be applied at the same time (e.g., in the same application), or may be applied in separate applications spaced in time such that they are effective at the same time. The bacteriophage may be applied as a single application, periodic applications, or as a continuous application.

Other bacteria within the contemplation of the present invention include, inter alia, *Campylobacter*, *E. coli* H7:0157, and *Listeria*, and *Staphylococcus*.

EXAMPLES

Example 1

Obtaining VRE Isolates

Isolation of VRE

VRE were isolated by standard methods from patients in the surgical intensive care and intermediate care units of the University of Maryland Medical Center in Baltimore. Trypticase Soy Agar supplemented with 5% sheep blood (BBL, Cockeysville Md.) was used to isolate enterococci from urine, wounds and sterile body fluids. VRE were isolated from stool specimens on Colistin Nalidixic Acid (CNA) agar (Difco labs, Detroit, Mich.) supplemented with defibrinated sheep blood (5%), vancomycin (10 g/ml) and amphotericin (1 g/ml). See Facklam, R. R., and D. F. Sahm. 1995. *Enterococcus*. In: Manual of Clinical Microbiology, 6$^{th}$ edition, American Society for Microbiology, Washington, D.C., pp. 508-312.

Identification of VRE

Enterococci were identified by esculin hydrolysis and growth in 6.5% NaCl at 45° C. Identification to the species level was done using conventional testing as indicated in Facklam and Collins (Facklam, et al. (1989), "Identification of *Enterococcus* species isolated from human infections by a conventional method test scheme." *J. Clin. Microbiol.*, 27:731-4).

Antimicrobial Susceptibility Testing of VRE

Antimicrobial susceptibilities to ampicillin, vancomycin, streptomycin, and gentamicin were determined using the E test quantitative minimum inhibitory concentration procedure (AB Biodisk, Solna Sweden). Quality control stains of *E. faecium* (ATCC 29212, 51299) were used to ensure potency of each antimicrobial agent tested. With exception of vancomycin, susceptibility interpretations from the National Committee for Clinical Laboratory Standards were adhered to (National Committee for Clinical Laboratory Procedures (1993), "Methods for Dilution Antimicrobial Susceptibility Tests for Bacteria that Grow Aerobically." 3rd Edition. National Committee for Clinical Laboratory Standards Villanova Pa.; National Committee for Clinical Laboratory Standards (1993), "Performance Standards for Antimicrobial Disk Susceptibility Tests" 5th Edition, National Committee for Clinical Laboratory Standards, Villanova Pa.). A VRE isolate was defined as one which had a minimum inhibitory concentration to vancomycin of at least 16 g/ml.

Defining Genetically Distinct VRE Strains

Distinct VRE isolates were characterized as such by contour-clamped homogeneous electric field electrophoresis after digestion of chromosomal DNA with SmaI (Verma, P. et al. (1994) "Epidemiologic characterization of vancomycin resistant enterococci recovered from a University Hospital" (Abstract). In; Abstracts of the 94th General Meeting of the American Society for Microbiology, Las Vegas Nev.; Dean, et al. (1994) "Vancomycin resistant enterococci (VRE) of the vanB genotype demonstrating glycoprotein (G) resistance inducible by vancomycin (V) or teicoplanin (T)" In; Abstracts of the 94th General Meeting of the American Society for Microbiology, Las Vegas Nev.). Electrophoretic studies were also performed using ApaI digestion for VRE strains which differed only by 1-3 bands after initial analysis (Donabedian, S. M. et al (1992) "Molecular typing of ampicillin-resistant, non-beta lactamase producing *Enterococcus faecium* isolates from diverse geographic areas." *J. Clin. Microbiol.* 30: 2757-61). The vancomycin-resistant genotype (vanA, vanB or vanC) was defined by polymerase chain reaction analysis using specific primers selected from published gene sequences (Goering, R. V. and the Molecular Epidemiological Study Group (1994) "Guidelines for evaluating pulsed field restriction fragment patterns in the epidemiological analysis of nosocomial infections." (Abstract) Third International Meeting of Bacterial Epidemiological Markers; Cambridge England).

Example 2

Isolation of VRE Phage 500 ml of raw sewage from the University of Maryland is mixed with 100 ml of 10 times concentrated LB broth (Difco Laboratories). This sewage-broth mixture is inoculated with a 18-24 hour LB broth culture (1 ml) of a VRE strain and incubated at 37° C. for 24 hours to enrich the mixture for bacteriophage which can infect the VRE strain added. After incubation, the mixture is centrifuged at 5000 g for 15 minutes to eliminate matter which may interfere with subsequent filtration. The supernatant is filtered through a 0.45 m Millipore filter. Filtrate is assayed using the Streak Plate Method and/or Appelman Tube Turbidity Test to detect lytic activity against different strains of VRE.

Method for Testing Phage Against VRE Isolates

Three methods are employed: Plaque Assay; Streak Plate Method; and Tube Turbidity Method, and the procedures for each follow.

Plaque Assay:

A 18-24 hour nutrient broth culture of the VRE strain (0.1 nil) to be tested for susceptibility to infection and dilutions of a VRE phage preparation (1.0 ml) are mixed and then added to 4.5 ml 0.7% molten agar in nutrient broth at 45° C. This mixture is completely poured into a petri dish containing 25 ml of nutrient broth solidified with 2% agar. During overnight incubation at 37° C., VRE grow in the agar and form a confluent lawn with some VRE cells being infected with phage. These phages replicate and lyse the initially infected cells and subsequently infect and lyse neighboring bacteria. However the agar limits the physical spread of the phage throughout the plate, resulting in small visibly clear areas called plaques on the plate where bacteriophage has destroyed VRE within the confluent lawn of VRE growth.

The number of plaques formed from a given volume of a given dilution of bacteriophage preparation is a reflection of the titer of the bacteriophage preparation. Also, since one plaque with a distinct morphology represents one phage particle that replicated in VRE in that area of the bacterial lawn, the purity of a bacteriophage preparation can be ensured by removing the material in that plaque with a pasteur pipette (a "plaque pick") and using this material as the inoculum for further growth cycles of the phage. On this basis, doing further plaque assays on preparations of phage grown from this plaque pick, one would expect all plaques to have a single appearance or plaque morphology which is the same as the plaque picked, a further indication of purity. Therefore this technique can not only be used to test bacteriophage potency but also bacteriophage purity.

Streak Plate Method:

Eighteen hour LB broth cultures of the different enterococci strains to be tested are grown at 37° C. (resulting in approximately 10$^9$ CFU/ml) and a loopful of each culture is streaked across a nutrient agar plate in a single line. This results in each plate having a number of different VRE streaked across it in single straight lines of growth. Single drops of phage filtrates to be tested are applied to the steaks of each VRE growth, and the plate is incubated 6 hours at 37° C., at which time the steaks of the different VRE strains are examined for the ability of phage to form clear areas devoid of bacterial growth, indicating lysis of that particular VRE strain by that particular phage.

The VRE host range for a given phage filtrate can be ascertained by which VRE streaks it is capable of causing a clear area devoid of growth and which strains of VRE the phage is incapable of doing this.

Appelman Tube Turbidity Test (from Adams, M. H. 1959. Bacteriophages. Interscience Publ. New York N.Y.):

18 hour LB broth cultures of different VRE strains are prepared. 0.1 ml of phage filtrate or a dilution thereof is added to 4.5 ml of VRE broth cultures and incubated at 37° C. for 4 hours (monophages) or 4-18 hours (polyvalent phages). Phage free VRE broth cultures are used as controls. Broth cultures which are normally turbid due to bacterial growth are examined for the ability of the phage to lyse the VRE strain as indicated by the clearing of the culture turbidity.

The host range of a given phage can be ascertained by which VRE broth cultures the phage is capable of clearing and which broth cultures it cannot induce clearing.

Example 3

A Phage Strain is Active Against Over 200 VRE Isolates

A collection of 234 VRE isolates, 187, *E. faecium* of which 3 strains are from ATCC, 41 *E. faecalis* strains, and 6 *E. gallinarium* strains as well as 6 *E. faecium* strains which are vancomycin sensitive were tested for susceptibility of infection by 7 monophages isolated as described in Example 2. Susceptibility of infection was determined by the 3 techniques described. The majority of VRE strains in this collection were isolated from patients at the University of Maryland and Baltimore VA Medical Centers as indicated in Example 1. Such VRE isolates were determined to be distinct and genetically diverse by pulsed field gel electrophoresis typing. Of the 7 monophages, VRE/E2 and VRE/E3 have a relatively narrow host range compared to other VRE phages, but are able to infect the small proportion of VRE strains which were resistant to other phages collected. A phage cocktail containing the above 7 VRE monophages lysed 95% of the VRE strains in the collection.

Example 4

Producing Bacteriophage-Containing Compositions 0.1 ml amounts of a 18-24 LB broth culture[1] of a strain of VRE, which has been previously selected on the basis of being able to produce a maximum yield of bacteriophage are mixed with 1.0 ml of a VRE monophage filtrate and then mixed with 4.5 ml of 0.7% molten agar in nutrient broth at 450 C. This mixture is completely poured into a petri dish containing 25 ml of nutrient broth solidified with 2% agar. After overnight incubation at 37° C., the soft top agar layer with the phage is recovered by gently scraping it off the plate, and this recovered layer is mixed with a small volume of broth (1 ml per plate harvested). This suspension is centrifuged at 5,000-6,000 g for 20 minutes at 4° C. and the phage containing supernatant is carefully removed. The supernatant is filtered through a 0.45 m filter and centrifuged at 30,000 g for 2-3 hours at 4° C.

[1] LB broth culture contains Bacto LB Broth. Miller (Luria-Bertani, dehydragted) reconstituted according to instructions by Difco Laboratories, Detroit, Mich.

The phage containing pellet is suspended in 1-5 ml of phosphate buffer and is further purified by ion exchange chromatography using a Q resource ion exchange column (Pharmacia Biotech Piscataway N.J.) and a 0-1 M NaCl gradient in the start buffer. Phage tends to be eluted from the column between 150-170 mM NaCl with each fraction being assessed for the presence of phage by standard plaque assay technique. Fractions collected and assayed are pooled if the phage titer by the plaque assay is no greater than 3 logs lower than the phage preparation put onto the column (e.g., $10^{10}$ PFU/ml is put onto the column therefore pool only those fractions with titers >$10^7$ PFU/ml). Pooled fractions are tested for endotoxin by the *Limulus Amebocyte* Lysate Assay (Bio-Whittaker Inc Walkersville Md.). Pools demonstrating, >50 EU/ml of endotoxin are passed through a Affi-prep polymyxin support column (Bio-Rad Labs, Hercules, Calif.) to remove residual endotoxin.

The phage pool is buffer exchanged against 100 mM ammonium bicarbonate using size exclusion with Sephadex G-25 chromatography (Pharmacia Biotech). 1 ml aliquots of the purified phage are freeze dried in the presence of gelatin and stored at room temperature. The purity of the phage preparation is assessed by a combination of electron microscopy, SDS-PAGE, DNA restriction digest and analytical ultracentrifugation.

Example 5

Determination of a Protective Dose of Bacteriophage

Establishment of Sustained VRE Colonization in a Animal Model

CD-1 mice are pretreated for seven days with 0.1 mg/ml of gentamicin and 0.5 mg/ml of streptomycin in drinking water to reduce their normal intestinal flora. VRE are then administered to the mice, who have fasted for 6 hours, by consumption of one food pellet inoculated with $10^6$ CFU of VRE. VRE intestinal colonization is confirmed in mice by standard colony counts of >$10^3$ CFU VRE/gram of feces on CNA agar containing 10 g/ml of vancomycin, 1 g/ml of amphotericin B and 10 g/ml of gentamicin. The colonization procedure is considered successful if there is consistent shedding of >$10^3$ CFU of VRE per gram of feces for 5-7 days after consumption of the spiked food pellet. VRE colonization may persist for 4 weeks by this method. Mice are given drinking water containing the above mixture of antibiotics throughout the duration of the experiment.

Use of a In Vivo Mouse Model to Demonstrate Efficacy of Lytic Bacteriophage in Reducing VRE Gastrointestinal Colonization.

Twenty-four hours after detecting >$10^3$ CFU VRE/grain of feces, mice were administered VRE phage (by having them consume one food pellet inoculated with $10^9$ PFU of VRE). Control groups consisted of (1) non-VRE-colonized mice sham dosed (no phage in dose), (2) VRE-colonized mice which are sham dosed, and (3) non-VRE-colonized mice dosed with phage. Five mice were used in each group.

The efficacy of phage treatment to reduce VRE gastrointestinal colonization was determined by quantitating VRE, on a daily basis, in weighed fecal samples from the mice in the different groups. In addition, at the end of the experiment, mice were sacrificed and the number of VRE and phage in their liver, spleen, and blood determined. If administration of phage reduced VRE gastrointestinal colonization/overall load in mice by at least 1 log as compared to the control groups within 48-98 hours after phage administration, then this dose of the particular phage was deemed efficacious. More preferably, colonization was reduced by at least 3 logs.

Example 6

Reduction of Colonization in Humans

The primary objective of this study is to (i) determine the efficacy of a candidate phage preparation in transiently eliminating/reducing VRE colonization in humans, and (ii) further assess the kinetics of turnover and the safety of the phages in immunocompromised patients, who are at greatest risk for VRE infections. The study is a double-blinded, placebo-controlled trial of oral phage administration in hospitalized patients colonized with VRE.

VRE-colonized patients are enrolled in the study. The patients are randomized to receive VRE-specific phages or a placebo. Stool samples are collected immediately before administration of the phages or placebo and 1, 2 and 3 days after administration of the phages or placebo; for patients who remain hospitalized, additional stool samples may be obtained 7 and 10 days after phage/placebo administration. The amount of VRE and VRE-specific phages in the stools is quantitated, and data is recorded on patient diagnosis, level of immunosuppression (as reflected by the degree of neutropenia or administration of immunosuppressive medications), and concurrent antibiotic therapy, if any. Side effects of phage administration, and changes in blood counts and renal and liver function are noted.

Sufficient patients should be enrolled in each arm of the study to enable detection of a significant difference between groups (95% confidence, 80% power) if 20% of the group receiving phages are VRE positive 3 days after phage administration, vs. 50% of the group receiving a placebo. For these early Phase II efficacy studies, VRE cases are selected which are susceptible to the phage preparation in vitro; a "broad spectrum" VRE phage preparation may be tested during subsequent, more randomized clinical trials (i.e., phase III clinical trials). VRE counts will be compared before and after phage/placebo administration, in order to determine whether phage administration, even if not eradicating carriage, results in a significant (>1 log) decrease in VRE levels in stools. All VRE isolates will be screened for susceptibility to the phage preparation. Most patients are expected to be colonized with only a single strain of VRE, some may have multiple strains; therefore, for a minimum of patients, 10-20 VRE colonies should be picked from the primary isolation plate, in order to assess clonality (by PFGE) and for screening for phage susceptibility.

A successful outcome for the studies consists of the demonstration that (i) significantly more patients receiving phages became VRE culture-negative than did patients receiving the placebo, or (ii) there was a significantly greater decrease (>1 log) in VRE levels in the stools of persons receiving phages as compared with persons receiving the placebo. From a clinical standpoint, there would be great value in reducing the levels of intestinal colonization during periods of severe neutropenia/immunosuppression, when the risk of bacteremia is greatest.

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in medicine, bacteriology, infectious diseases, pharmacology, and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention claimed is:

1. A method for reducing the risk of bacterial infection or sepsis in a person colonized with pathogenic bacteria comprising treating the colonized person with a pharmaceutical composition containing bacteriophage of one or more strains which produce lyric infections in said pathogenic bacteria, wherein said treatment occurs prior to said colonized person developing an illness due to said pathogenic bacteria and said treatment reduces the risk of bacterial infection or sepsis in said colonized person, and wherein said treatment of the colonized person reduces the level of colonization with pathogenic bacteria susceptible to the bacteriophage by at least one log, wherein said composition is administered intravesicularly, topically, orally, rectally, ocularly, otically, nasally, or via inhalation.

2. The method of claim 1, wherein the colonized person is an immunocompromised patient selected from the group consisting of leukemia patients, lymphoma patients, carcinoma patients, sarcoma patients, allogeneic transplant patients, congenital or acquired immunodeficiency patients, cystic fibrosis patients, and AIDS patients.

3. The method of claim 1, wherein the pathogenic bacteria are selected from the group consisting of vancomycin-resistant enterococcus (VRE), pneumococcal species, methicillin-resistant *Staphylococcus aureus*, multi-drug resistant *Staphylococcus aureus* (MDRSA), multi-drug resistant *Pseudomonas* species, *Nesseria* sp., *Hemophilus* sp., *Proteus* sp., *Klebsiella* sp. and *Esherichia coli*.

4. The method of claim 3, wherein the pathogenic bacteria are selected from the group consisting of VRE, MDRSA, and multi-drug resistant *Pseudomonas*.

5. The method of claim 1, wherein the bacteriophage composition is selected from the group consisting of an oral tablet, capsule or liquid, a nasal aerosol, a throat wash, a mouth wash or gargle, a toothpaste, and a topical ointment.

6. The method of claim 1, wherein the colonized person is a person having a wound selected from the group consisting of an ulcer, a laceration, a deep penetrating wound and a surgical wound, and the bacteriophage produce lytic infections in pathogenic bacteria capable of infecting these wounds.

7. The method of claim 6, wherein the composition is a topical ointment, an irrigation solution or a component of a wound dressing.

8. The method of claim 1, wherein the pharmaceutical composition contains a plurality of bacteriophage strains.

9. The method of claim 8, wherein the pharmaceutical composition contains bacteriophage strains which produce lytic infections in pathogenic bacteria of a plurality of bacterial strains.

10. The method of claim 8, wherein the pharmaceutical composition contains bacteriophage strains which produce lytic infections in pathogenic bacteria of a plurality of bacterial species.

11. The method of claim 2, wherein the pathogenic bacteria are selected from the group consisting of VRE, MDRSA, and multi-drug resistant *Pseudomonas* species.

12. The method of claim 6, wherein the pathogenic bacteria are selected from the group consisting of methicillin-resistant *Staphylococcus aureus* and MDRSA.

13. The method of claim 1, wherein the bacteriophage composition is selected from the group consisting of tampons, rinses, creams, and aerosols.

14. A method for reducing the incidence of infection by selected pathogenic bacteria in a medical facility comprising administering to patients admitted to the medical facility a bacteriophage preparation which reduces the colonization level by the selected pathogenic bacteria in patients at risk for infection by the selected pathogenic bacteria, wherein said colonization level is reduced by at least one log, wherein said bacteriophage preparation is administered intravesiculady, topically, orally, rectally, ocularly, otically, nasally, or via inhalation.

15. The method of claim 14, wherein the patients at risk for infection are selected from the group consisting of leukemia patients, lymphoma patients, carcinoma patients, sarcoma patients, allogeneic transplant patients, congenital or acquired immunodeficiency patients, cystic fibrosis patients, and AIDS patients.

16. The method of claim 12, wherein said bacteriophage preparation is administered to substantially all patients admitted to said medical facility.

17. The method of claim 14, wherein said bacteriophage preparation is administered to substantially all patients colonized with the selected bacteria who are admitted to said medical facility.

18. The method of claim 14, wherein the selected pathogenic bacteria is VRE, MDRSA, or multi-drug resistant *Pseudomonas*.

19. The method of claim 15, wherein the selected bacteria is VRE, MDRSA, or multi-drug resistant *Pseudomonas*.

20. The method of claim 14, wherein the composition is selected from the group consisting of an oral tablet, capsule or liquid, a nasal aerosol, a throat wash, a mouth wash or gargle, a toothpaste, and a topical ointment.

21. The method of claim 14, wherein the bacteriophage composition is selected from the group consisting of tampons, rinses, creams, and aerosols.

22. A method for reducing the level of colonization in a patient comprising treating the patient with a composition containing bacteriophage of one or more strains which produce lyric infections in pathogenic bacteria, wherein said patient is colonized with the pathogenic bacteria subject to infection by said bacteriophage, and wherein said treatment of the patient reduces the level of colonization with pathogenic bacteria susceptible to the bacteriophage by at least one log, wherein said composition is administered intxavesicularly, topically, orally, rectally, ocularly, otically, nasally, or via inhalation.

23. The method of claim 22, wherein the susceptible patient is an immunocompromised patient selected from the group consisting of leukemia patients, lymphoma patients, carcinoma patients, sarcoma patients, allogeneic transplant patients, congenital or acquired immunodeficiency patients, cystic fibrosis patients, and AIDS patients.

24. The method of claim 22, wherein the pathogenic bacteria are selected from the group consisting of VRE, pneumococcal species, methicillin-resistant *Staphylococcus aureus*, MDRSA, multi-drug resistant *Pseudomonas* species, *Nesseria* sp., *Hemophilus* sp., *Proteus* sp., *Klebsiella* sp. and *Esherichia coli*.

25. The method of claim 24, wherein the pathogenic bacteria are selected from the group consisting of VRE, MDRSA, and multi-drug resistant *Pseudomonas*.

26. The method of claim 22, wherein the composition is selected from the group consisting of an oral tablet, capsule or liquid, a nasal aerosol, a throat wash, a mouth wash or gargle, a toothpaste, and a topical ointment.

27. The method of claim 22, wherein the patient has a wound selected from the group consisting of an ulcer, a laceration, a deep penetrating wound and a surgical wound, and the bacteriophage produce lytic infections in pathogenic bacteria capable of infecting these wounds.

28. The method of claim 27, wherein the composition is a topical ointment, an irrigation solution or a component of a wound dressing.

29. The method of claim 22, wherein the composition contains a plurality of bacteriophage strains.

30. The method of claim 29, wherein the composition contains bacteriophage strains which produce lytic infections in pathogenic bacteria of a plurality of bacterial strains.

31. The method of claim 29, wherein the composition contains bacteriophage strains which produce lytic infections in pathogenic bacteria of a plurality of bacterial species.

32. The method of claim 23, wherein the pathogenic bacteria are selected from the group consisting of VRE, MDRSA, and multi-drug resistant *Pseudomonas* species.

33. The method of claim 27, wherein the pathogenic bacteria are selected from the group consisting of methicillin-resistant *Staphylococcus aureus* and MDRSA.

34. The method of claim 24, wherein the pathogenic bacteria is VRE.

35. The method of claim 24, wherein the pathogenic bacteria is MDRSA.

36. The method of claim 24, wherein the pathogenic bacteria is multi-drug resistant *Pseudomonas* species.

37. The method of claim 35, wherein the composition is a nasal spray.

38. The method of claim 36, wherein the composition is a mouth wash or gargle.

39. The method of claim 22, wherein the bacteriophage composition is selected from the group consisting of tampons, rinses, creams, and aerosols.

* * * * *